(12) United States Patent
Bjällmark et al.

(10) Patent No.: US 8,996,093 B2
(45) Date of Patent: Mar. 31, 2015

(54) SYSTEM TO QUANTIFY AND VISUALIZE VENTRICULAR ROTATION PATTERN OF THE HEART

(76) Inventors: Anna Bjällmark, Solna (SE); Ulf Gustafsson, Umeå (SE); Lars-Åke Brodin, Täby (SE); Anders Waldenström, Stockholm (SE); Matilda Larsson, Huddinge (SE)

( * ) Notice: Subject to any disclaimer, the term of this patent is extended or adjusted under 35 U.S.C. 154(b) by 294 days.

(21) Appl. No.: 13/492,502

(22) Filed: Jun. 8, 2012

(65) Prior Publication Data

US 2012/0302870 A1 Nov. 29, 2012

Related U.S. Application Data

(63) Continuation of application No. PCT/EP2010/069408, filed on Dec. 10, 2010.

(30) Foreign Application Priority Data

Dec. 10, 2009 (SE) ...................................... 0901546

(51) Int. Cl.
| | |
|---|---|
| A61B 5/02 | (2006.01) |
| A61B 8/08 | (2006.01) |
| A61B 8/06 | (2006.01) |
| A61B 8/13 | (2006.01) |
| G06T 7/00 | (2006.01) |
| G06T 7/20 | (2006.01) |
| A61B 5/055 | (2006.01) |

(52) U.S. Cl.
CPC .................. *A61B 8/0883* (2013.01); *A61B 8/06* (2013.01); *A61B 8/13* (2013.01); *A61B 8/488* (2013.01); *G06T 7/0012* (2013.01); *G06T 7/2046* (2013.01); *A61B 5/055* (2013.01); *A61B 8/485* (2013.01); *G06T 2207/10132* (2013.01); *G06T 2207/30048* (2013.01)
USPC ............ 600/410; 600/443; 600/453; 382/128

(58) Field of Classification Search
USPC ........................... 600/410, 443, 453; 382/128
See application file for complete search history.

(56) References Cited

U.S. PATENT DOCUMENTS

| | | | | |
|---|---|---|---|---|
| 2005/0261577 | A1* | 11/2005 | Ficaro et al. ................... | 600/425 |
| 2007/0092123 | A1* | 4/2007 | Popescu ........................ | 382/128 |
| 2007/0203420 | A1* | 8/2007 | Belalcazar et al. ........... | 600/512 |
| 2008/0009734 | A1* | 1/2008 | Houle et al. ................... | 600/443 |

* cited by examiner

*Primary Examiner* — Baisakhi Roy
(74) *Attorney, Agent, or Firm* — Birch, Stewart, Kolasch & Birch, LLP

(57) ABSTRACT

A non-invasive analysis system includes data collecting units and an analysis unit adapted to quantify and visualize ventricular rotation patterns of the heart. The data collecting units register rotational information about the cardiac movement for a number of time points and levels in the heart throughout the cardiac cycle. The analysis unit calculates rotation planes for different levels in the heart over time and constructs rotation planes from at least two rotation lines originating from the same level in the heart. Each of the rotation lines are created between a pair of points having matching rotation values located in ventricular walls, and to calculate a rotation axis for the rotation plane for each selected level. The analysis unit creates a model of the rotational pattern of the heart. Deflection and direction of the rotation axes for the rotation planes at selected levels of the ventricles are quantified and visualized.

20 Claims, 6 Drawing Sheets

US 8,996,093 B2

SYSTEM TO QUANTIFY AND VISUALIZE VENTRICULAR ROTATION PATTERN OF THE HEART

CROSS REFERENCE TO RELATED APPLICATIONS

This application is a continuation of PCT/EP2010/069408 filed on Dec. 10, 2010, which claims priority under 35 U.S.C. 119(a) to Patent Application No. 0901546-2 filed in Sweden on Dec. 10, 2009, all of which are hereby expressly incorporated by reference into the present application.

FIELD OF THE INVENTION

The present invention relates to a system according to the preamble of the independent claim.

BACKGROUND OF THE INVENTION

When describing left ventricular (LV) function by echocardiography, the main focus has been to study the longitudinal and radial motion. However, a third motion that recently has gained interest is the circumferential (rotational) motion of the LV.

Different modalities have been used to describe this motion and studies have indicated LV twist to be an additional integral component in LV function (Buchalter et al. 1994; Moon et al. 1994; Dong et al. 1999; Tibayan et al. 2004). Other studies have provided detailed information on the twisting motion of the LV, by measuring regional and segmental as well as endocardial and epicardial rotation (Gustafsson et al. 2009; Goffinet et al. 2009). So far, only amplitudes of rotation have been reported, whereas the rotation pattern of the LV has not been fully described.

Earlier studies have shown systolic clockwise rotation at the base and counterclockwise rotation at the apex of the LV, creating a twist (Stuber et al. 1999; Notomi et al. 2005; Takeuchi et al. 2006). Therefore, between the opposite directions of rotation at the base and the apex, there must be a transition level with no rotation. In a previous study, a rotation of zero degrees could be measured in only one or two segments simultaneously at one level of the LV in the short-axis image in healthy subjects (Gustafsson et al. 2009). This indicates that the image plane was not parallel to the transition plane, which also means that the axis of rotation at the transition level was not congruent to the longitudinal axis, presuming the short-axis images were perpendicular to the LV longitudinal axis.

The object of the present application is to achieve a system that presents a novel way to quantify and visualize the ventricular rotation pattern of the heart.

The present invention is aimed to be used in the routine clinical practice at cardiology departments to improve the diagnostics of different cardiac diseases, through easy interpretable quantification and visualization of the rotation pattern of the left and right ventricles.

SUMMARY OF THE INVENTION

The above-mentioned object is achieved by the present invention according to the independent claim.

Preferred embodiments are set forth in the dependent claims.

The non-invasive analysis system, according to the present invention, comprises one or more data collecting units and an analysis unit, which analysis unit is adapted to quantify and visualize ventricular rotation pattern of the heart. The one or more data collecting units are adapted to register rotational information about the cardiac movement for a number of time points and for a number of levels in the heart throughout the cardiac cycle and said analysis unit is adapted to calculate rotation planes for different levels in the heart over time, and to construct rotation planes from at least two rotation lines originating from the same level in the heart, and wherein each of the rotation lines are created between a pair of points having matching rotation values located in ventricular walls, and to calculate a rotation axis for the rotation plane for each selected level, and that said analysis unit further is adapted to create a model of the rotational pattern of the heart, wherein deflection and direction of the rotation axes for the rotation planes at selected levels of the ventricles are quantified and visualized.

According to the present invention, first, non-invasive image acquisition is required to collect rotation values from different positions of the myocardium. Thereafter, a kinematic model of the ventricles is constructed in order to determine the rotation planes at different levels of the heart and to identify the transition level of the ventricles. The orientations of the rotation planes over time are visualized by plotting the motion of the normal vectors of the rotation planes, i.e. the rotation axis of the planes.

The invention presents a novel non-invasive way to assess the rotation axis of a ventricle. This provides further insight into the complexity of ventricular function and uniquely describes the cardiac rotation pattern, since all available techniques today only focus on single rotational amplitude values and not on how the ventricles rotate. This new method is different to all other method used today for assessing cardiac function, as it does not describe the amplitude of a motion but the relationship in motions between different parts within a ventricle. This invention introduces a new concept and new parameters to evaluate ventricular function and provides a unique overview of the rotation pattern of the ventricles.

SHORT DESCRIPTION OF THE APPENDED DRAWINGS

Figure 4:
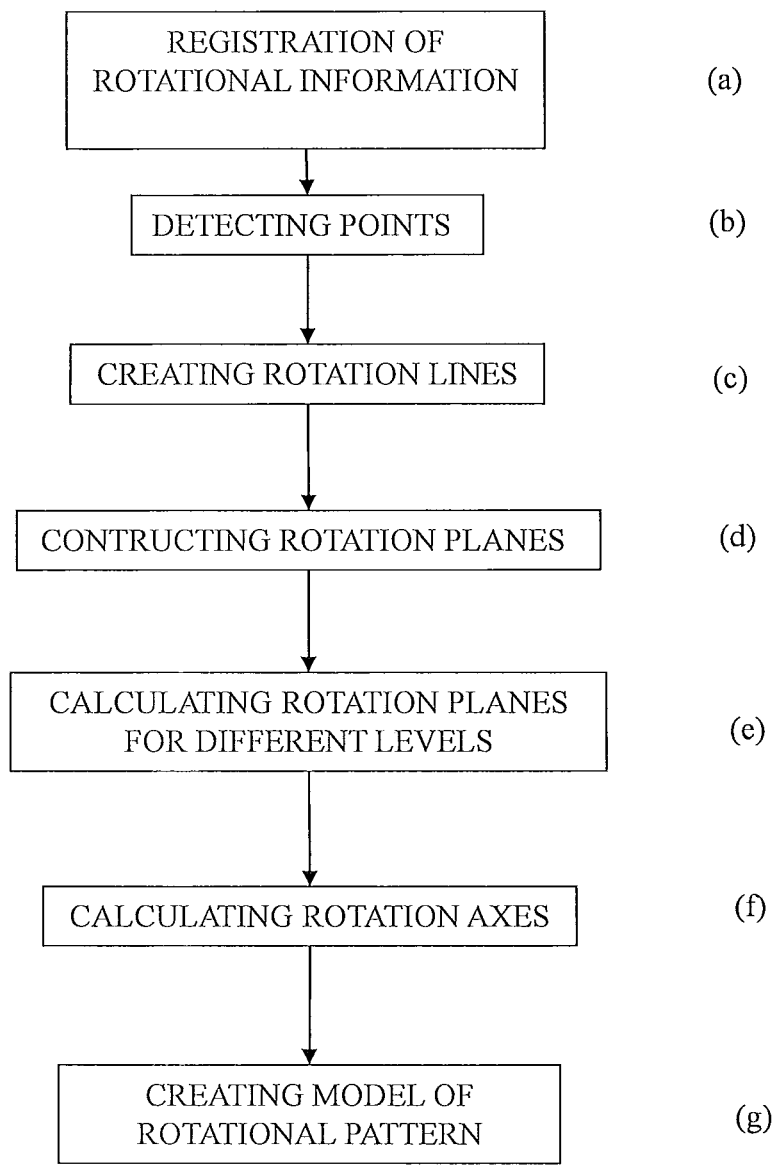

FIG. 4 schematically shows the method for quantifying and visualizing ventricular rotation pattern of the heart, according to the present invention.

Figure 5:
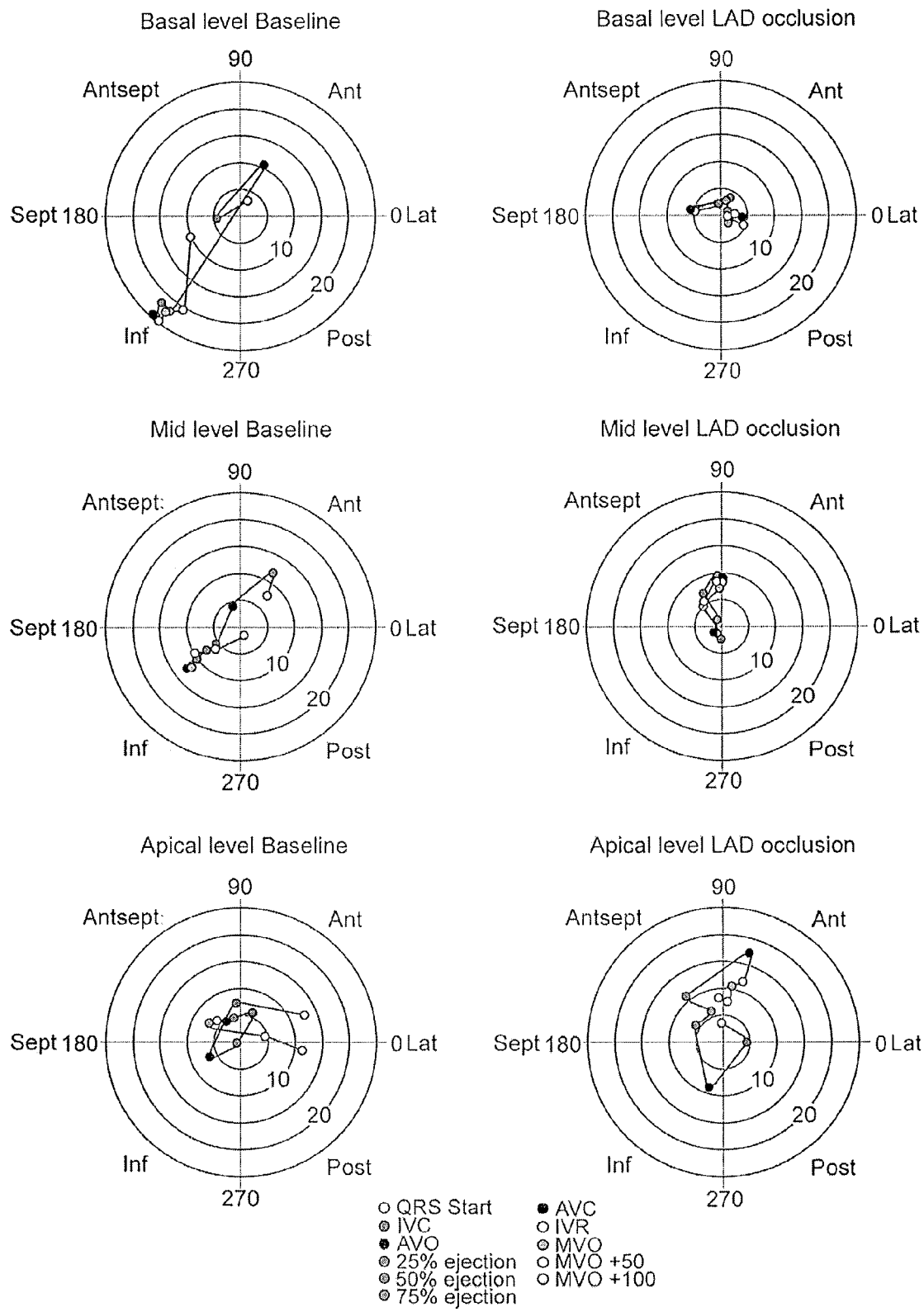

FIG. 5 shows the results of the rotation axis at baseline and after acute regional ischemia in the LV in 6 pigs.

Figure 6:
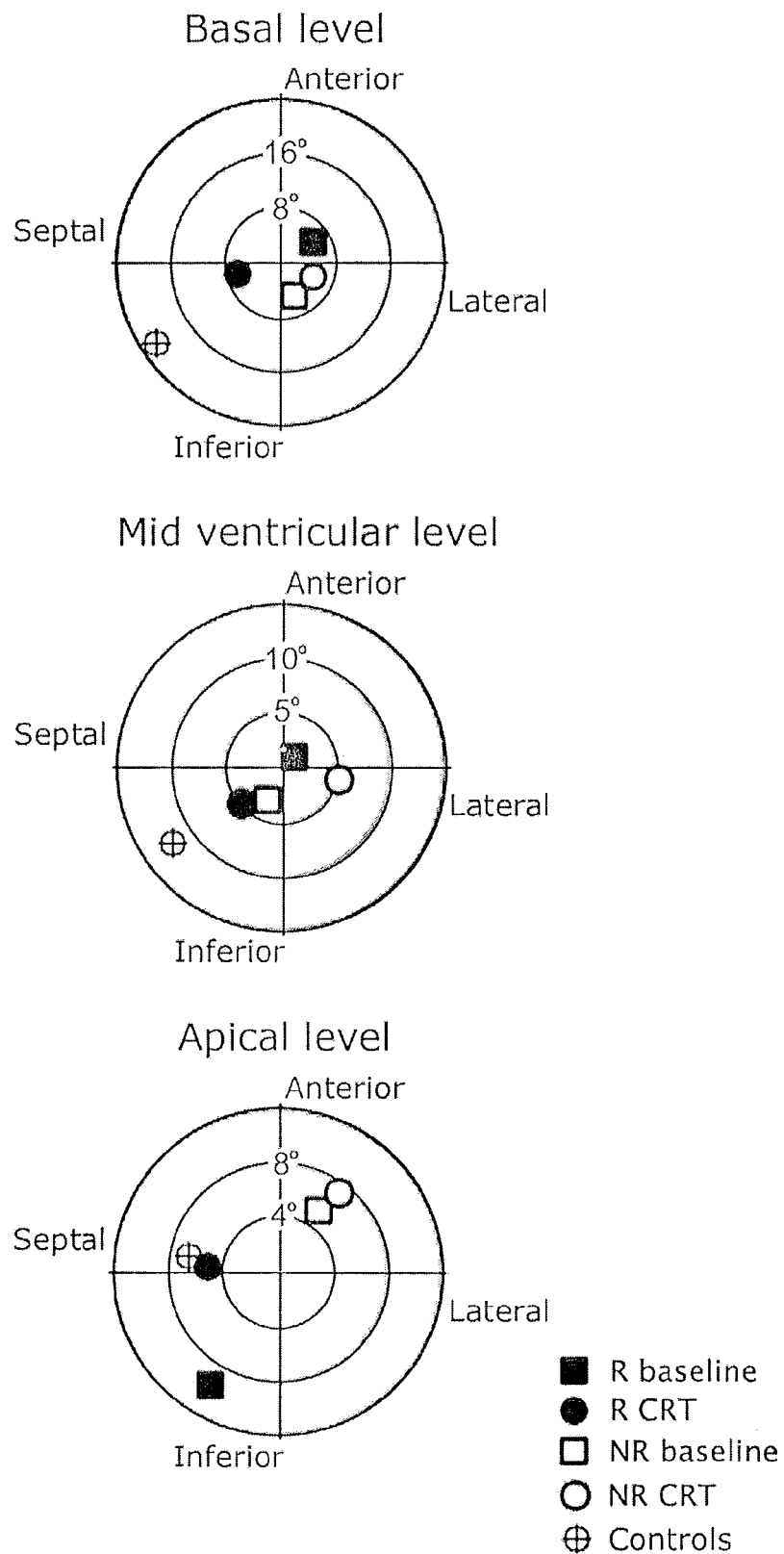

FIG. 6 shows the results of the rotation axis at baseline and after cardiac resynchronization therapy (CRT) in responders and non-responders to CRT.

DETAILED DESCRIPTION OF PREFERRED EMBODIMENTS OF THE INVENTION

Figure 1:
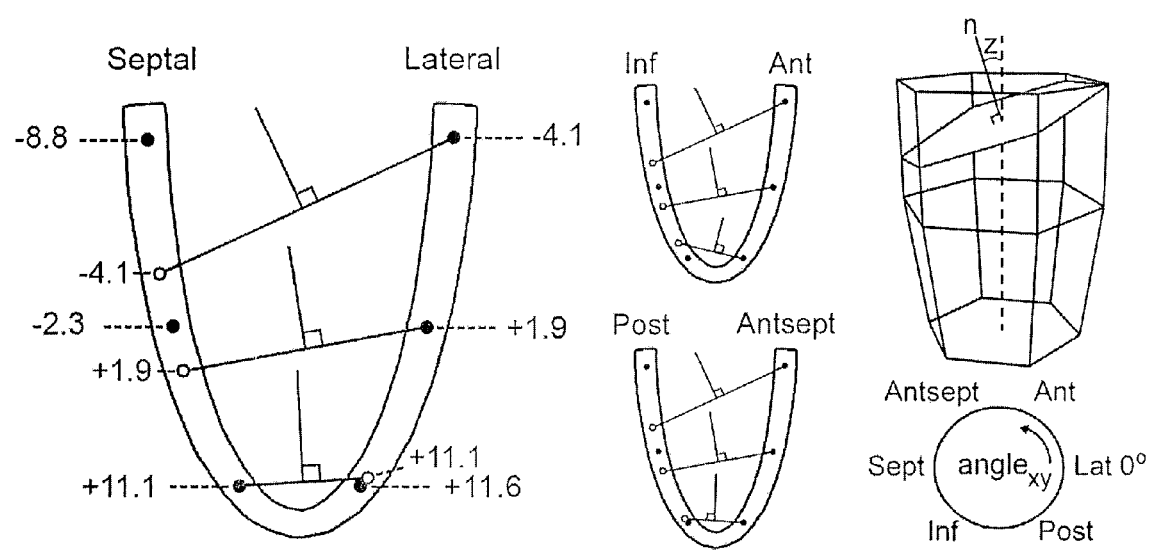
FIG. 1 shows a schematic description of a rotation plane calculation in the analysis unit, according to the present invention.

FIG. 1 shows a schematic description of a rotation plane calculation. The illustrations to the left and in the middle show the LV from three apical long-axis views. The black filled dots represent points with measured rotation values, the small unfilled dots represent a matching rotation value (by interpolation) in the opposite wall to one of the measured rotation values at each level. The line between a pair of matching points represents a rotation line, which is displayed as a black straight line between opposite walls in the Figure. The illustration to the upper right displays the primary model with 18 coordinates (intersections of the black lines) and a calculated rotation plane as a mean of the calculated rotation lines at the basal level. The normal vector to the plane (n) is the rotation axis of the rotation plane. The deflection of the rotation axis is described by $angle_z$, relative to the longitudinal axis of the LV. The direction of the rotation axis in the xy-plane is described by $angle_{xy}$, which is defined as 0° at the lateral wall with increasing angles counterclockwise (see lower right). Ant, anterior; Lat, lateral; Post, posterior; Inf, inferior; Sept, septal; Antsept, anteroseptal.

Figure 2:
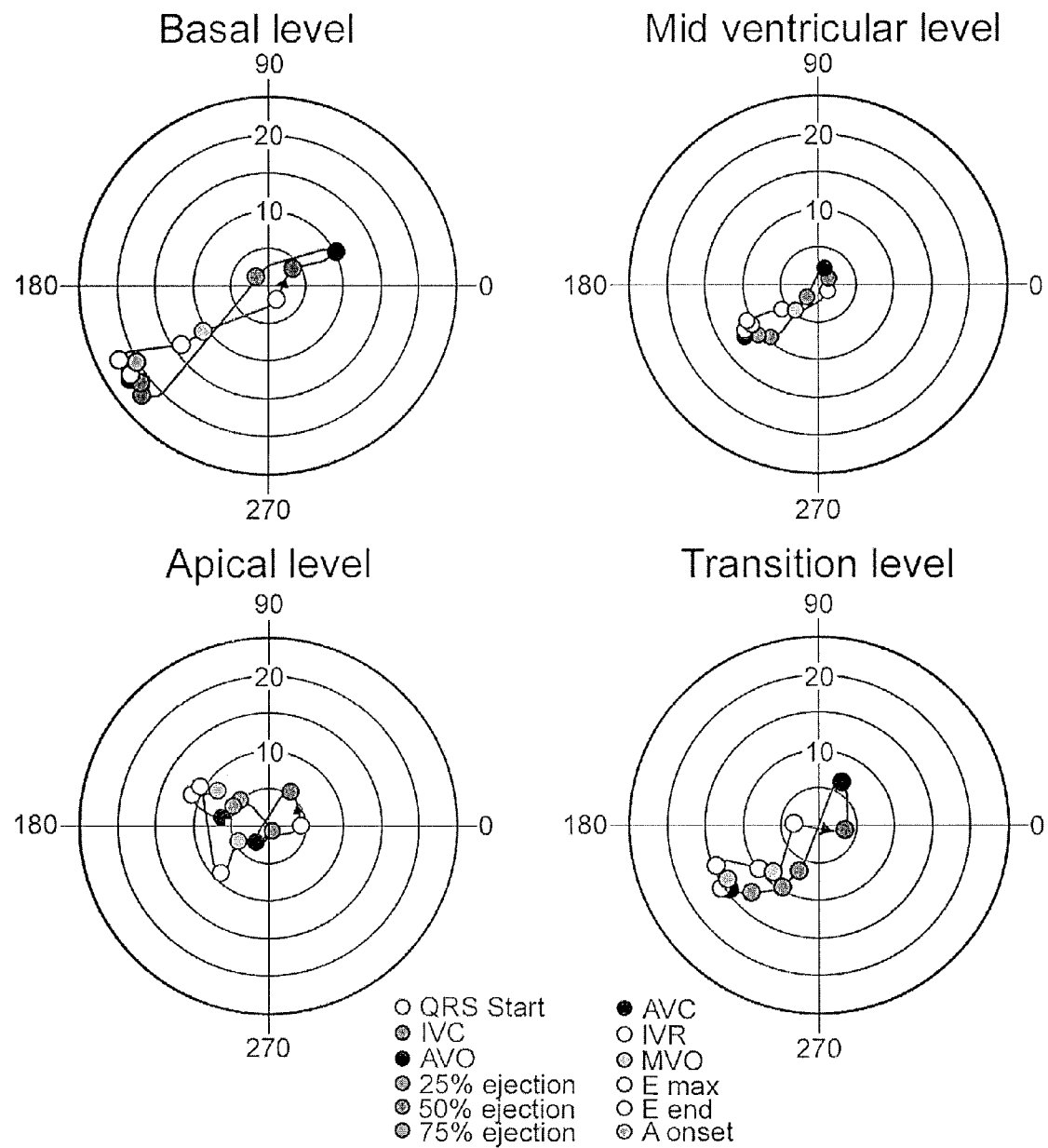
FIG. 2 shows an example of how the visualization of the motion pattern of the rotation axes is performed in the analysis unit, according to the present invention.

FIG. 2 shows mean deflection ($angle_z$,°), represented by the axial scale in the plots, and mean direction ($angle_{xy}$,°), represented by the circular scale in the plots, of the calculated rotation axes in 39 healthy subjects presented for discrete time points throughout the cardiac cycle at basal, mid-, apical and transition levels. Every discrete point has been color-coded as defined below the tomograms. Ant, anteroseptal; ant, anterior; lat, lateral; post, posterior; inf, inferior; sept, septal. IVC, mid-isovolumic contraction; AVO, aortic valve opening; AVC, aortic valve closure; IVR, mid-isovolumic relaxation; MVO, mitral valve opening; E-peak, peak velocity of early diastolic filling; E-end, end of early diastolic filling; A-onset, start of atrial wave.

Figure 3:
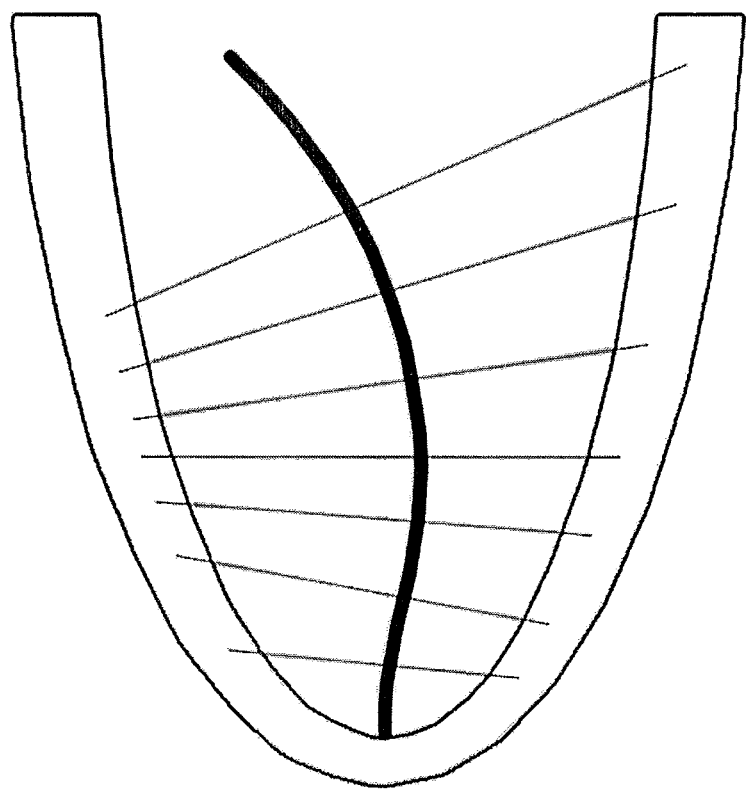
FIG. 3 illustrates the mean global torsion axis of the left ventricle, according to an embodiment of the present invention.

FIG. 3 illustrates the left ventricle (LV) with the mean torsion axis of 39 healthy subjects at end systole. The torsion axis is perpendicular to the rotation planes at any specific level and represents the rotation axis of the entire LV. It is based on the rotation planes at three levels (basal, mid- and apical levels).

FIG. 5 shows the results of the rotation axis at three levels of the LV in 6 pigs at baseline and after 4 minutes of left anterior descending coronary artery occlusion. The orientation of the rotation axis is displayed in the circular and linear graphs where deflection is presented in the axial scale as the distance from the centre and the direction is presented in the circular scale, where also anatomical positions are marked.

FIG. 6 shows the position of the rotation axis at end of systole in 19 patients that have cardiac resynchronization therapy (CRT). The circular and linear graphs show both the mean results at baseline and after CRT in responders (R) and non-responders (NR) to CRT as well as in 39 healthy humans.

In this part the invention will be described in detail. The invention relates to a non-invasive analysis system to quantify and visualize the rotation pattern of ventricles of the heart. The analysis system comprises two subsystem where subsystem 1 is a data collecting unit and subsystem 2 is an analysis unit. The data collecting unit includes one or many non-invasive image generating means, or the data collecting unit facilitates registration of variables quantifying the rotation pattern of the ventricles. There exist different techniques to perform the registrations. One example is the ultrasound technique, which will be described in the following. Subsystem 2, the analysis unit, performs the calculation of rotation planes and rotation axes by constructing a model of the ventricles based upon rotation parameters registered by subsystem 1. The construction of a model is shown in FIG. 1 and will be described for the left ventricle of the heart. Subsystem 2 also includes a visualization unit where the motion patterns of the rotation axes are displayed in axial-circular plots. Subsystem 2 may be separate or may be integrated in subsystem 1. Some definitions are listed below to simplify the understanding of the detailed description of the system.

The data collecting system may be an ultrasound system using a reflector-based technique, an ultrasound system using a Doppler-technique, a magnetic resonance tomography system, or any imaging system with ability to quantify rotation amplitudes.

DEFINITIONS

Rotation line—a line between a pair of points with similar rotation values located in two opposite ventricular walls in an apical long-axis view of the LV, where at least one point is located at either the basal, mid- or apical level, see FIG. 1.

Rotation plane—a plane constructed by at least two rotation lines originating from the same level, see FIG. 1.

Rotation axis—the central normal vector of a rotation plane, i.e. the axis around which the LV rotates in a rotation plane, see FIG. 1.

Transition plane—a rotation plane with rotation values close to zero.

Deflection—the angle between a rotation axis and the longitudinal axis of the LV, defined as $angle_z$ in FIG. 1 to the upper right.

Direction—the direction of a rotation axis in the transverse plane of the LV, defined as $angle_{xy}$ with 0° at the lateral wall and increasing angles counter-clockwise, see FIG. 1 to the lower right.

zlevel—the distance in percent between the apex and the mean z-coordinate of a rotation or transition plane, where 0% corresponds to the apex and 100% to the base.

Twist-ratio—the ratio of apical rotation to sign-reversed basal rotation.

Image Acquisition and Offline Analysis

The image acquisition can be performed with different 2D or 3D imaging modalities, such as ultrasound and magnetic resonance tomography. The image acquisition will here be explained according to the 2D ultrasound technique. Standard echocardiographic short-axis images at basal, mid-ventricular and apical levels, as well as apical four-chamber views are recorded using an ultrasound system. End-systolic and end-diastolic diameters are measured in each short-axis image as well as the approximate distance to each level in respect to the apex in the apical images. Time to aortic valve closure (AVC) is measured from the beginning of QRS as reference time for end of systole. Regional rotation of the ventricular wall, divided in three or more segments, is analyzed at each short-axis level using a commercial software for wall motion analysis. In our example the analyzed region was divided into six segments. The beginning and end of the analysis is set at the start of QRS in the superimposed ECG including one cardiac cycle.

To use the rotation data from the rotation analysis, each rotation analysis is exported to a text file, where the rotation is presented in degrees as the mean of each segment at every sampled frame.

Development of Rotation Axis Software

The rotation axis software is based on a simplified model of the LV that is constructed from the 18 geometric measuring points describing the six segments in short-axis views at the basal, mid- and apical levels and the distances from the apex to each level (FIG. 1). The rotation data and geometric data are imported to Matlab 7.0.1 (MathWorks Inc., Natick, Mass., USA) where the rotation axis software was developed. Every rotation value is assigned an xyz-coordinate, with z along the longitudinal axis of the LV and x, y in the short-axis plane of the LV. This results in a primary model of 18 coordinates with both a position and a rotation value, one every 60 degrees in the short-axis plane at the three levels (FIG. 1). Additionally, the time from the Q-wave in the ECG to AVC is added in the data input for analyzing the rotation axis. The software is initiated by automated selection of one cardiac cycle, by the identification of the time of zero rotation, which is the same as the defined cardiac cycle in the speckle tracking analysis. The geometry change during the cardiac cycle is accounted for in the model by setting end-diastolic diameters at the start and end of the cardiac cycle and by setting end-systolic diameters at the time of AVC. In between those measured diameters, linear interpolation in time is applied to obtain coordinates throughout the cardiac cycle. To create a model with high spatial resolution, linear interpolation is applied in the longitudinal direction to generate coordinates every 0.1 mm between the basal, mid- and apical levels.

Thereby, every coordinate in the model is given a rotation value at every sampled frame throughout the cardiac cycle, using linear interpolation between the 18 measured values of rotation. Between opposite sides, as in each apical long-axis view, one pair of points with similar rotation values is selected (one by measurement and the other by interpolation) to define a rotation line, see FIG. 1. The rotation line originated from one of the two measured rotation values at each level. In the case of two possible rotation lines, the rotation line that best corresponded to small difference in rotation values with a mean z-coordinate close to the addressed level is selected to influence the calculation of the rotation plane at this level. The selection procedure of rotation lines can generally be described as follows. If the pair of points of both rotation lines had less than 0.05° difference in rotation values, the rotation line with the mean z-coordinate nearest the corresponding level is selected. If no rotation line satisfied this first criterion, the line with the smallest difference in rotation values is selected, if the difference in rotation values is smaller than 0.5°. If the difference is not smaller than 0.5° for any line, no line is selected from that level, and is considered a missing value. When two or three rotation lines between opposite walls originating from the same level can be selected, a rotation plane at that specific level can be calculated.

Three coordinates are the minimum number needed to define a plane. The six coordinates from the three lines are condensed to three coordinates that are used to calculate a rotation plane, according to (1-3), where $ant_{(x,y,z)}$, $antsept_{(x,y,z)}$, $sept_{(x,y,z)}$, $post_{(x,y,z)}$, $lat_{(x,y,z)}$, were the xyz-coordinate for each selected point, referring to its wall position.

$$P_1 = \frac{ant_{(x,y,z)} - antsept_{(x,y,z)}}{2} \quad (1)$$

$$P_2 = \frac{sept_{(x,y,z)} - inf_{(x,y,z)}}{2} \quad (2)$$

$$P_3 = \frac{post_{(x,y,z)} - lat_{(x,y,z)}}{2} \quad (3)$$

The plane constructed by the points $P_1$, $P_2$ and $P_3$ is defined as the plane of rotation at the corresponding level. If one of the xyz-coordinates is missing, the corresponding mean point, $P_1$, $P_2$ or $P_3$, becomes equal to the non-missing xyz-coordinate. If both xyz-coordinates are missing in one of the equations 1-3, the corresponding mean point is assigned a xyz-coordinate from one of the other equations 1-3. The xyz-coordinate that replaces the mean point that could not be calculated is then discarded in the equation where it is originally included. To express the motion pattern of the rotation plane, the normal vector to the plane (n), i.e. the rotation axis, is calculated as the cross product of the two vectors $V_1$ and $V_2$ between the points $P_1$, $P_2$ and $P_3$ according to (4-6).

$$V_1 = P_1 - P_2 \quad (4)$$

$$V_2 = P_1 - P_3 \quad (5)$$

$$n = V_1 \times V_2 = \det \begin{bmatrix} x & y & z \\ V_{1,x} & V_{1,y} & V_{1,z} \\ V_{2,x} & V_{2,y} & V_{2,z} \end{bmatrix} \quad (6)$$

The deflection ($angle_z$) and direction ($angle_{xy}$) of the rotation axis are then calculated as:

$$angle_z = \frac{\cos^{-1}(dot(\hat{z}, n))}{|n|} \quad (7)$$

$$angle_{xy} = \tan^{-1} \frac{n_y}{n_x} \quad (8)$$

A transition plane describing a level in the LV with rotation values close to zero is also calculated. This plane is calculated in the same way as the planes at the three levels by using the equations 1-8. The xyz-coordinate in each wall is obtained by identifying the zero-coordinates, i.e. the coordinates where the rotation values shifts from positive to negative.

Furthermore, the present invention also relates to a method for quantifying and visualizing ventricular rotation pattern of the ventricle, as illustrated in FIG. 4. The method includes:
 a) registration of rotational information about the cardiac movement for a number of time points and for a number of levels in the heart throughout the cardiac cycle,
 b) detecting points located in the ventricular walls having matching rotation values,
 c) creating rotation lines between said pair of points,
 d) constructing rotation planes from at least two rotation lines originating from the same level in the heart, or from at least three coordinates,
 e) calculating rotation planes for a number of different levels in the heart over time,
 f) calculating a rotation axis for each rotation plane for each selected level,
 g) creating a model of the rotational pattern of the heart, wherein deflection and direction of the rotation axes for the rotation planes at selected levels of the ventricles are quantified and visualized.

According to one embodiment of the present invention, the method for quantifying and visualizing ventricular rotation pattern of the heart further includes the sub step:
 h) calculating a curved rotation axis influenced by the rotation axes at every level of the left ventricle, i.e. a global torsion axis of the left ventricle.

Preliminary Results

In one study, the rotation axis software was applied in a group of 39 healthy individuals and in a patient with anteroseptal myocardial infarction. The deflection and direction of the rotation axes were calculated in every recorded image frame throughout the cardiac cycle and presented at 12 time points, see FIG. 2. The deflections of the axes were greatest at the basal level in most of the time points throughout the cardiac cycle and were, in general, least pronounced at the mid-level. The deflection of the rotation axes differed significantly from zero in all tested time points, i.e. the rotation axes were not congruent to the longitudinal axis of the LV. The Rayleigh's tests for uniformity demonstrated significant mean directions of the rotation axes for the majority of the tested time points. The rotation axis at basal and mid levels was directed towards the inferoseptal area during late systole and early diastole and showing only small variations during this period. At the apical level the axis was directed towards the anteroseptal area, also with only small variations during this period. This indicates that there was a uniform change in rotation throughout the ventricle during late systole and early diastole, even though most of the rotation of the ventricle occurred during this period. This shows that this method does not describe the amplitude of rotation but the relationship in rotation between different pars of the ventricle. FIG. 2 visualizes the mean deflection (axial) and direction (circular) of the rotation axis at three levels of the LV and at the transition level in the 39 healthy subjects for the 12 selected time points. Moreover, the position of the transition plane, defined as the distance in percent between the apex and the rotation plane, 0%=apex, 100%=base, was investigated and the mean transition plane was located at the upper part of the papillary muscles (60-65% of ventricle length) during most of the cardiac cycle. The direction and deflection of the axis of the transition plane resembled both mid and basal levels. Additionally, the present method showed acceptable reproducibility, except at the apical level, where there were small differences in rotation between the segments which made the axis more sensitive to regional changes of rotation. The quality measures showed relatively small differences in rotation values between the segments within one rotation plane.

In an experimental animal study we investigated the effect of acute regional ischemia on the rotation pattern of the LV. Six anesthetized pigs were examined using ultrasound equipment before (baseline) and four minutes after we induced regional ischemia by occluding the left anterior descending coronary artery (LAD). From the ultrasound images, measurements of rotation and longitudinal function were also done in addition to the measurements needed to calculate the rotation axis at different levels of the LV. At baseline the motion of the rotation axis at all three levels were very much like the rotation pattern seen in healthy humans, indicating a normal functioning heart. After LAD occlusion the rotation pattern of the LV had changed. The rotation axis changed from being directed towards the inferoseptal area at basal and mid levels at baseline to being directed towards the anterior area after LAD occlusion. There was a significant difference in the direction of the rotation axis at all three levels and a significant difference in deflection at basal and apical levels (FIG. 5). Also, a significant difference in the symmetry of the rotational motion during late systole and early diastole was found at both basal and apical levels. This indicates that the rotation pattern did not only change after LAD occlusion but it also became less symmetric, meaning that the changes in regional rotation was not uniform. No significant changes in conventional measurements of rotation could be found. However, a significant difference in longitudinal function, assessed by AV-plane displacement, was seen at the lateral wall and a borderline significant difference at the lateral wall, indicating that AV-plane displacement seems sensitive to changes in regional function but may not be so specific in describing the affected area. In this study the rotation axis was as sensitive as AV-plane displacement in detecting ischemia but has in difference the potential to localize the area with reduced function.

In a third study we have investigated the response of the rotation axis to cardiac resynchronization therapy (CRT) in 19 patients. Normally there are only about ⅔ of the patients receiving CRT that responds positive to the treatment. In about ⅓ there is no improvement of the patients cardiac function. The 19 patients were divided into 13 responders and 6 non-responders to CRT based on a 6 minutes walk test. Ultrasound (echocardiographic) images of the heart were recorded before implantation (baseline) and after 3 months with active CRT. In addition to standard echocardiographic measurements, conventional measurements of rotation and the rotation axis was also measured. The rotation axis of the patients was compared to the 39 healthy humans in study 1. At baseline there were no significant differences between responders and non-responders. After CRT a significant difference in fractional shortening and AV-plane displacement was found, supporting the selection of responders and non-responders. In either responders or non-responders there were no significant differences in rotation or twist amplitudes or in time to peak rotation at basal and apical levels between baseline and after CRT. However, the rotation axis showed a clear tendency of becoming more normalized at all three levels in responders and a significant difference in the direction of the rotation axis was found when combining the basal and mid levels (FIG. 6). In non-responders there was a tendency of the rotation axis becoming more pathological at all three levels, however no significant differences was found. This study indicates that the rotation pattern is changed by CRT, in especially patients responding positively to CRT. Changes in the rotation pattern could only be detected by the method of assessing the rotation axis and not by conventional measurements of rotation. The results also indicate that studying the rotation axis could help in optimizing CRT settings.

The novel system and method introduces a new concept to evaluate LV function, by estimating planes of rotation at different levels of the LV and by describing the motion pattern of the rotation axes. We have demonstrated that the LV does not rotate around its longitudinal axis in normal conditions, but around another axis, the direction of which changes in a complex manner during the cardiac cycle. By displaying data on deflection and direction of the rotation axis at different levels, a unique overview of the rotation pattern of the LV is achieved. Using this new method we can now, for the first time, describe the transition plane of the ventricle. The preliminary results indicate that the rotation axis method is more sensitive than conventional measurements of ventricular rotation to changes in the rotation pattern. It also has the ability to assess the symmetry of the circumferential motion of the whole ventricle, which is also unique.

The differences in direction and deflection of the axes during pre-ejection and ejection might indicate different rotational functions of the subendocardial and the subepicardial layers, presuming each myocardial layer is the main contributor in the respective phases.

The rotation axes were directed towards the anterolateral area during pre-ejection, which could be an effect of the early activation of subendocardial fibers. During the ejection phase, when the subepicardial fibers are supposedly responsible for most of the twisting motion, the direction of the axes changed towards the outflow area.

The orientation of the rotation axis remains stationary as long as there is a uniform change of rotation in all segments of the LV. However, if the rotation in one or a few segments alters in respect to other segments, the orientation of the axis in space will differ.

The results indicate that this new method is more sensitive than present methods in detecting dysfunction of the ventricular rotation pattern. The system and method is advantageous in that it describes the circumferential movement pattern of the entire ventricle and not only regional movement pattern within the ventricle.

Therefore, this method seemed suitable for differentiating stable from unstable rotation patterns, where a stable rotation pattern describes uniform changes in rotation amplitudes. Moreover, absence of a transition plane indicates that all levels of the LV are rotating in the same direction, meaning that there is no effective twist. Absence and the position of the transition plane might both be markers of dysfunction. Clear differences in rotation pattern between the healthy group and the patient with ischemia and anteroseptal post infarction were seen. Thus, this new method could be used for early detection of cardiac diseases and for selection of patients for and optimization of cardiac resynchronization therapy.

The present invention is not limited to the above-described preferred embodiments. Various alternatives, modifications and equivalents may be used. Therefore, the above embodiments should not be taken as limiting the scope of the invention, which is defined by the appending claims.

REFERENCES

Arts T, Meerbaum S, Reneman R S, Corday E. Torsion of the left ventricle during the ejection phase in the intact dog. *Cardiovasc Res* 1984; 18:183-93.

Buchalter M B, Rademakers F E, Weiss J L, Rogers W J, Weisfeldt M L, Shapiro E P. Rotational deformation of the canine left ventricle measured by magnetic resonance tagging: effects of catecholamines, ischaemia, and pacing. *Cardiovasc Res* 1994; 28:629-35.

Dong S J, Hees P S, Huang W M, Buffer S A, Jr., Weiss J L, Shapiro E P. Independent effects of preload, afterload, and contractility on left ventricular torsion. *Am J Physiol* 1999; 277:H1053-60.

Goffinet C, Chenot F, Robert A, Pouleur A C, le Polain de Waroux J B, Vancrayenest D, Gerard O, Pasquet A, Gerber B L, Vanoverschelde J L. Assessment of subendocardial vs. subepicardial left ventricular rotation and twist using two-dimensional speckle tracking echocardiography: comparison with tagged cardiac magnetic resonance. *Eur Heart J* 2009; 30:608-17.

Greenbaum R A, Ho S Y, Gibson D G, Becker A E, Anderson R H. Left ventricular fibre architecture in man. *Br Heart J* 1981; 45:248-63.

Gustafsson R A, Lindqvist P, Morner S, Waldenstrom A. Assessment of regional rotation patterns improves the understanding of the systolic and diastolic left ventricular function: an echocardiographic speckle-tracking study in healthy individuals. *Eur J Echocardiogr* 2009; 10.56-61.

Ingels N B, Jr., Hansen D E, Daughters G T, 2nd, Stinson E B, Alderman E L, Miller D C. Relation between longitudinal, circumferential, and oblique shortening and torsional deformation in the left ventricle of the transplanted human heart. *Circ Res* 1989; 64:915-27.

Jin S M, Noh C I, Bae E J, Choi J Y, Yun Y S. Decreased left ventricular torsion and untwisting in children with dilated cardiomyopathy. *Journal of Korean medical science* 2007; 22:633-40.

Moon M R, Ingels N B, Jr., Daughters G T, 2nd, Stinson E B, Hansen D E, Miller D C. Alterations in left ventricular twist mechanics with inotropic stimulation and volume loading in human subjects. *Circulation* 1994; 89:142-50.

Notomi Y, Lysyansky P, Setser R M, Shiota T, Popovic Z B, Martin-Miklovic M G, Weaver J A, Oryszak S J, Greenberg N L, White R D, Thomas J D. Measurement of ventricular torsion by two-dimensional ultrasound speckle tracking imaging. *J Am Coll Cardiol* 2005; 45:2034-41.

Sengupta P P, Khandheria B K, Korinek J, Wang J, Belohlavek M. Biphasic tissue Doppler waveforms during isovolumic phases are associated with asynchronous deformation of subendocardial and subepicardial layers. *J Appl Physiol* 2005; 99:1104-11.

Streeter D D, Jr., Spotnitz H M, Patel D P, Ross J, Jr., Sonnenblick E H. Fiber orientation in the canine left ventricle during diastole and systole. *Circ Res* 1969; 24:339-47.

Stuber M, Scheidegger M B, Fischer S E, Nagel E, Steinemann F, Hess O M, Boesiger P. Alterations in the local myocardial motion pattern in patients suffering from pressure overload due to aortic stenosis. *Circulation* 1999; 100:361-8.

Takeuchi M, Nakai H, Kokumai M, Nishikage T, Otani S, Lang R M. Age-related changes in left ventricular twist assessed by two-dimensional speckle-tracking imaging. *J Am Soc Echocardiogr* 2006; 19:1077-84.

Tibayan F A, Rodriguez F, Langer F, Zasio M K, Bailey L, Liang D, Daughters G T, Ingels N B, Jr., Miller D C. Alterations in left ventricular torsion and diastolic recoil after myocardial infarction with and without chronic ischemic mitral regurgitation. *Circulation* 2004; 110:11109-14.

Uznanska B, Chrzanowski L, Plewka M, Lipiec P, Krzeminska-Pakula M, Kasprzak J D. The relation-ship between left ventricular late-systolic rotation and twist, and classic parameters of ventricular function and geometry. *Kardiologia polska* 2008; 66:740-7; discussion 8-9.

van Dalen B M, Soliman O I, Vletter W B, Kauer F, van der Zwaan H B, ten Cate F J, Geleijnse M L. Feasibility and reproducibility of left ventricular rotation parameters measured by speckle tracking echocardiography. *Eur J Echocardiogr* 2009; 10:669-76.

The invention claimed is:

1. A non-invasive analysis system, comprising one or more data collecting units and an analysis unit, which analysis unit is adapted to quantify and visualize ventricular rotation pattern of the heart wherein said one or more data collecting units are adapted to register rotational information about the cardiac movement for a number of time points and for a number of levels in the heart throughout the cardiac cycle and said analysis unit is adapted to calculate rotation planes for different levels in the heart over time, and to construct rotation planes from at least two rotation lines originating from the same level in the heart, and wherein each of the rotation lines are created between a pair of points having matching rotation values located in ventricular walls, and to calculate a rotation axis for the rotation plane for each selected level, and said analysis unit further is adapted to create a model of the rotational pattern of the heart, wherein deflection and direction of the rotation axes for the rotation planes at selected levels of the ventricles are quantified and visualized.

2. System according to claim 1, wherein said rotation planes are constructed from at least three rotation lines originating from the same level in the heart.

3. System according to claim 2, wherein said ventricular walls are opposite in relation to each other.

4. System according to claim 2, wherein said analysis unit is separate or integrated into the data collecting unit.

5. System according to claim 2, wherein said data collecting system is an ultrasound system using a reflector-based technique.

6. System according to claim 1, wherein said ventricular walls are opposite in relation to each other.

7. System according to claim 3, wherein said analysis unit is separate or integrated into the data collecting unit.

8. System according to claim 6, wherein said data collecting system is an ultrasound system using a reflector-based technique.

9. System according to claim 1, wherein said analysis unit is separate or integrated into the data collecting unit.

10. System according to claim 9, wherein said data collecting system is an ultrasound system using a reflector-based technique.

11. System according to claim 1, wherein said data collecting system is an ultrasound system using a reflector-based technique.

12. System according to claim 1, wherein said data collecting system is an ultrasound system using a Doppler-technique.

13. System according to claim 1, wherein said data collecting system is any imaging system with ability to quantify rotation amplitudes.

14. System according to claim 1, wherein said data collecting system is a magnetic resonance tomography system.

15. System according to claim 1, wherein said analysis unit visualizes the motion of the rotation axis at any level of the ventricles in axial-circular plots.

16. System according to claim 1, wherein said analysis unit presents data on where the transition level is located in the ventricles.

17. System according to claim 1, wherein said analysis unit quantifies and visualizes a global torsion axis of the left ventricle, i.e. the curved rotation axis influenced by the rotation axes at every level of the left ventricle.

18. System according to claim 1, wherein one of the points defining said rotation line for a selected level is created by means of measuring and the other by interpolation.

19. Method for quantifying and visualizing ventricular rotation pattern of the ventricle, including:
   a) registration of rotational information about the cardiac movement for a number of time points and for a number of levels in the heart throughout a cardiac cycle,
   b) detecting a pair of points located in the ventricular walls having matching rotation values,
   c) creating rotation lines between said pair of points,
   d) constructing rotation planes from at least two rotation lines originating from the same level in the heart,
   e) calculating rotation planes for a number of different levels in the heart over time,
   f) calculating a rotation axis for each rotation plane for each selected level,
   g) creating a model of the rotational pattern of the heart, wherein deflection and direction of the rotation axes for the rotation planes at selected levels of the ventricles are quantified and visualized.

20. Method for quantifying and visualizing ventricular rotation pattern of the heart according to claim 19, including the sub step of:
   h) calculating a curved rotation axis influenced by the rotation axes at every level of the left ventricle, i.e. a global torsion axis of the left ventricle.

* * * * *